(12) United States Patent
Gorny

(10) Patent No.: US 7,585,850 B2
(45) Date of Patent: Sep. 8, 2009

(54) STABLE AND ACTIVE COMPLEXES OF ADENOSINE AND ADENOSINE PHOSPHATES WITH AMINOALCOHOLS FOR THE TREATMENT OF PULMONARY ARTERY HYPERTENSION, CARDIAC FAILURE AND OTHER DISEASES

(75) Inventor: Philipe Gorny, Paris (FR)

(73) Assignee: Adenobio N.V., Schiphol (NL)

( * ) Notice: Subject to any disclaimer, the term of this patent is extended or adjusted under 35 U.S.C. 154(b) by 521 days.

(21) Appl. No.: 11/052,844

(22) Filed: Feb. 9, 2005

(65) Prior Publication Data

US 2005/0176675 A1   Aug. 11, 2005

(51) Int. Cl.
A61K 31/205 (2006.01)
A61K 31/70 (2006.01)
A61K 31/13 (2006.01)

(52) U.S. Cl. .......................... 514/46; 514/47; 514/554; 514/667

(58) Field of Classification Search .................. None
See application file for complete search history.

(56) References Cited

U.S. PATENT DOCUMENTS

| | | | |
|---|---|---|---|
| 3,088,871 A * | 5/1963 | Pfeiffer ................ 514/555 |
| 3,646,007 A | 2/1972 | Gordon |
| 3,993,639 A | 11/1976 | Mauvernay |
| 4,221,909 A | 9/1980 | Simon et al. |
| 4,221,910 A | 9/1980 | Giner-Sorolla |
| 6,444,234 B1 * | 9/2002 | Kirby et al. .............. 424/725 |
| 2003/0139368 A1 | 7/2003 | Gorny et al. |

FOREIGN PATENT DOCUMENTS

| | | |
|---|---|---|
| GB | 879259 A | 10/1961 |
| JP | 58140100 A2 | 8/1983 |

OTHER PUBLICATIONS

Morgan, J.M., "Adenosine as a Vasodilator in Primary Pulmonary Hypertension", Circulation, Sep. 1991, 1145-9, 84(3).
Fullerton, D.A., "Adenosine Effectively Controls Pulmonary Hypertension After Cardiac Operations," Ann Thorac Surg., Apr. 1996, 1118-23, 61(4).
Kitakaze, M. et al., "Adenosine Therapy: A New Approach to Chronic Heart Failure", Expert Opin Investig Drugs, Nov. 2000, 2519-35, 9(11).
Joshi, S., et al., "In Nonhuman Primates Intracarotid Adenosine, but not Sodium Nitroprusside, Increases Cerebral Blood Flow", Anesth Analg., Feb. 2002, 393-9, 94(2).
Dunwiddie, T.V. et al., "The Role and Regulation of Adenosine in the Central Nervous System", Annu. Rev. Neurosci, 2001, 31-55, 24.
Porkka-Heiskanen, T. et al., "Adenosine: A Mediator of the Sleep-Inducing Effects of Prolonged Wakefulness", Science, May 23, 1997, 1265, 276.
Ph. De Witte, Pinto, E., Ansseau, M. and Verbanck, P., "Alcohol and Withdrawal; From Animal Research to Clinical Issues", Neuroscience & Biobehavioral Reviews, 2003, 189-197, 27.
Lee, F.S. et al., Distinctive Features of Trk Neurotrophin Receptor Transactivation by G Protein-Coupled Receptors: Cytokine Growth Factor Rev., Feb. 2002, 11-7, 13(1).
Ferroni, S. et al., J. Neurosci Res., Jun. 1, 2002, 615-21, 68(5).
Ohta, A. et al., "Role of G-Protein-Coupled Receptors in Downregulation of Inflammation and Protection From Tissue Damage", Nature, 2001, 916-920, 414.
Cronstein, B.N., "Adenosine, An Endogeneous Anti-Inflammatory Agent", J Appl Physiol, Jan. 1994, 5-13, 76(1).
Zidek, Z., "Adenosine Cyclic AMP Pathways and Cytokine Expression" Review-European Cytokine Network, Sep. 1999, 319-28, 10(3).
Agteresch, H.J., et al., "Adenosine Triphosphate. Established and Potential Clinical Applications", Drugs, Aug. 1999, 211-232, 58(2).
Haskell, C.M. et al., "Phase I Trial of Extracellular ATP in Patients with Advanced Cancer", Med Pediatr Oncol, 1996, 165-73, 27(3).
Steele, D.S. et al., "Metabolic Factors Contributing to Altered Ca2+ Regulation in Skeletal Muscle Fatigue", Acta Phsiol Scand, Sep. 2003, 39-48, 179(1).
Harmer, A.R., "Skeletal Muscle Metabolic and Ionic Adaptations During Intense Exercise Following Sprint Training in Humans", J Appl Physiol, Nov. 2000, 1793-803, 89(5).
Forsyth, L.M., "Therapeutic Effects of Oral NADH on the Symptoms of Patients with Chronic Fatigue Syndrome", Ann Allergy Asthma Immunol., Feb. 1999, 185-91, 82(2).
Ventura-Clapier, R., "Metabolic Myopathy in Heart Failure", News Physiol Sci., Oct. 2002, 191-6, 17.
Ventura-Clapier, R. et al., "Energy Metabolism in Heart Failure", Physiol, Feb. 15, 2004, 1-13, 555(Pt 1), Epub Dec. 5, 2003.
Van Aken, H., et al., "Haemodynamic and Cerebral Effects of ATP-Induced Hypotension", Br J Anaesth, Dec. 1984, 1409-16, 56(12).

* cited by examiner

Primary Examiner—Traviss C McIntosh, III
(74) Attorney, Agent, or Firm—Dechert LLP

(57) ABSTRACT

The invention is directed to compositions and methods which permit the oral use of adenosine and adenosine phosphates for cardiovascular applications such as pulmonary artery hypertension, cardiac failure and other diseases. Certain compositions in accordance with the invention have enhanced AMP gastrointestinal bioavailability and thus efficacy. The invention prolongs the activity of adenosine and adenosine phosphates when administered intravenously. In particular, the invention contemplates methods of treating several human (as well as animal) cardiovascular and neurological medical conditions that could be improved by an effective amount of adenosine, ATP or AMP combined with dialkylaminoalcohols and their salts.

12 Claims, 17 Drawing Sheets

Figure 1. Adb-011 synthesis (330A2)
Synthetic pathway:
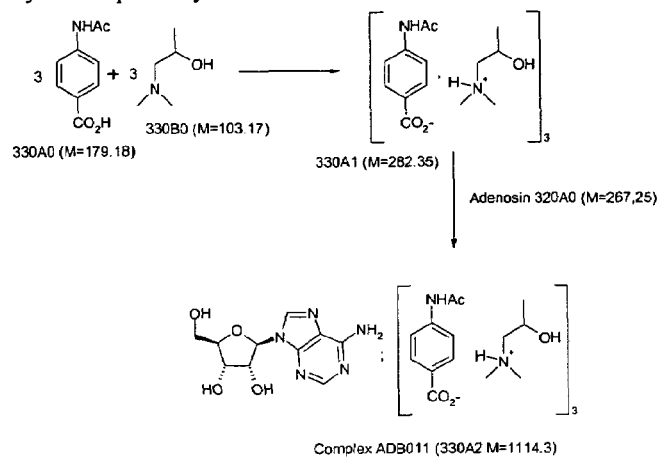
Step 1: formation of 330A1
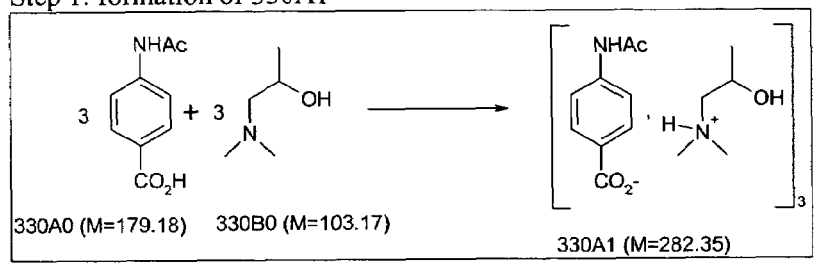
Quantities:
| Nom | MW g/mol | nbre de mole | rapport molaire | masse introduite en g | densité | volume ml | Rdt Théo. g |
|---|---|---|---|---|---|---|---|
| 330A0 | 179,2 | 2,79E-02 | 1,00 | 5,00 | | | |
| 330B0 | 103,2 | 0,03 | 1,0 | 2,9 | 1,082 | 2,7 | |
| H2O | 18,0 | 1,40 | 50,0 | 25,1 | 1,000 | 25,1 | |
| 330A1 | 282,35 | | | | | | 7,88 |
Step 2: formation of 330A2 (Adb011)
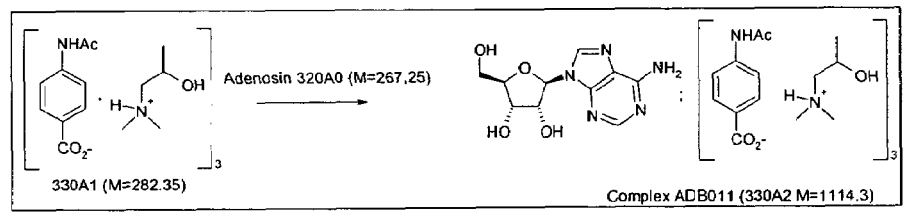
Quantities:
| Nom | MW g/mol | nbre de mole | rapport molaire | masse introduite en g | densité | volume ml | Rdt théo. g |
|---|---|---|---|---|---|---|---|
| 320A0 | 267,3 | 1,87E-03 | 1,00 | 0,50 | | | |
| 330A1 | 282,4 | 0,01 | 3,0 | 1,6 | | | |
| H2O | 18,0 | 0,09 | 50,0 | 1,7 | 1,000 | 1,7 | |
| 330A2 | 1114,3 | | | | | | 2,08 |

Figure 2. Adb311 & 111 synthesis
Adb 311 (330G1) synthetic pathway :
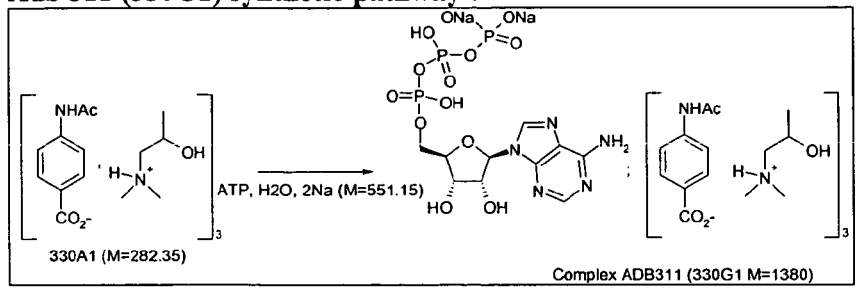
Quantities:
| Nom | MW g/mol | nbre de mole | rapport molaire | masse introduite en g | densité | volume ml | Rdt théo. g |
|---|---|---|---|---|---|---|---|
| ATP, H2O, 2Na | 551,2 | 9,07E-04 | 1,00 | 0,50 | | | |
| 330A1 | 282,4 | 0,00 | 3,0 | 0,8 | | | |
| H2O | 18,0 | 0,05 | 50,0 | 0,8 | 1,000 | 0,8 | |
| 330G1 | 1380 | | | | | | 1,25 |
Adb 111 (330E1) synthetic pathway:
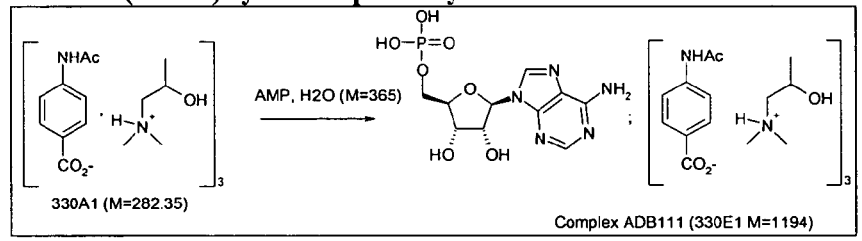
Quantities:
| Nom | MW g/mol | nbre de mole | rapport molaire | masse introduite en g | densité | volume ml | Rdt théo. g |
|---|---|---|---|---|---|---|---|
| AMP, H2O | 365,0 | 1,37E-03 | 1,00 | 0,50 | | | |
| 330A1 | 282,4 | 0,00 | 3,0 | 1,2 | | | |
| H2O | 18,0 | 0,07 | 50,0 | 1,2 | 1,000 | 1,2 | |
| 330E1 | 1194 | | | | | | 1,64 |

Figure 3a. Adb013 synthesis (330F0= Adipic acid)
Adb 013 (330F2) synthetic pathway:
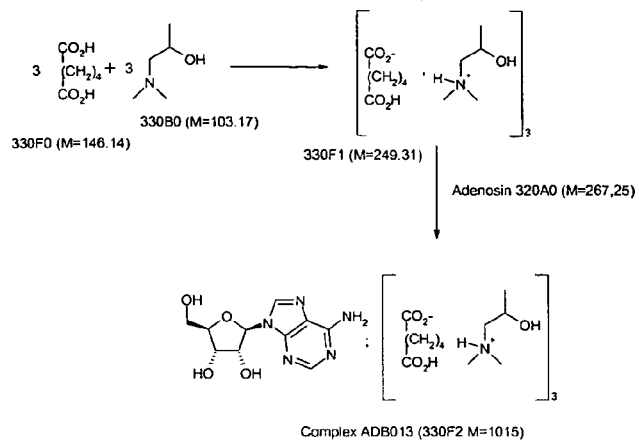
Step 1 : formation of 330F1
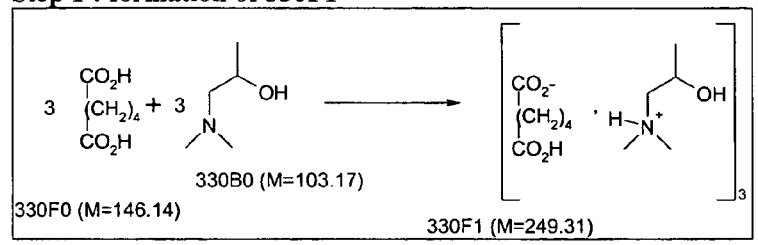
Quantities:
| Nom | MW g/mol | nbre de mole | rapport molaire | masse introduite en g | densité | volume ml | Rdt Théo. g |
|---|---|---|---|---|---|---|---|
| 330F0 | 146,1 | 3,42E-02 | 1,00 | 5,00 | | | |
| 330B0 | 103,2 | 0,03 | 1,0 | 3,5 | 1,082 | 3,3 | |
| H2O | 18,0 | 1,71 | 50,0 | 30,8 | 1,000 | 30,8 | |
| 330F1 | 249,31 | | | | | | 8,53 |
Step 2: formation of Adb013 (330F2)
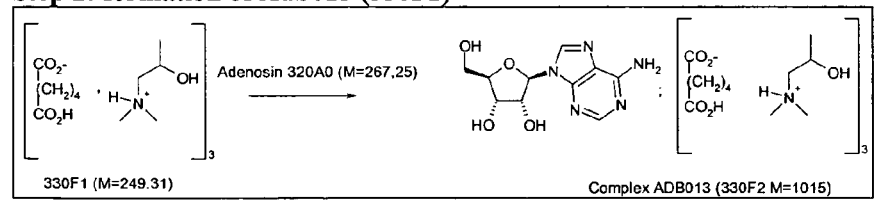
Quantities:
| Nom | MW g/mol | nbre de mole | rapport molaire | masse introduite en g | densité | volume ml | Rdt théo. g |
|---|---|---|---|---|---|---|---|
| 320A0 | 267,3 | 1,87E-03 | 1,00 | 0,50 | | | |
| 330F1 | 249,3 | 0,01 | 3,0 | 1,4 | | | |
| H2O | 18,0 | 0,09 | 50,0 | 1,7 | 1,000 | 1,7 | |
| 330F2 | 1015 | | | | | | 1,90 |

Figure 3b Adb-012 synthesis (330D0 = acetyl salicylic acid)
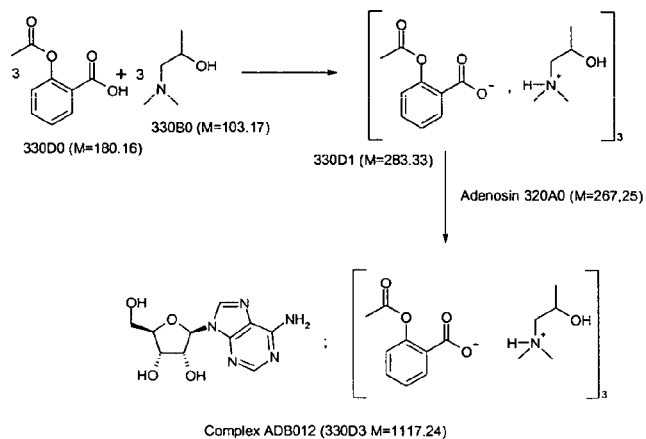
Figure 3c Synthesis of Adb-112
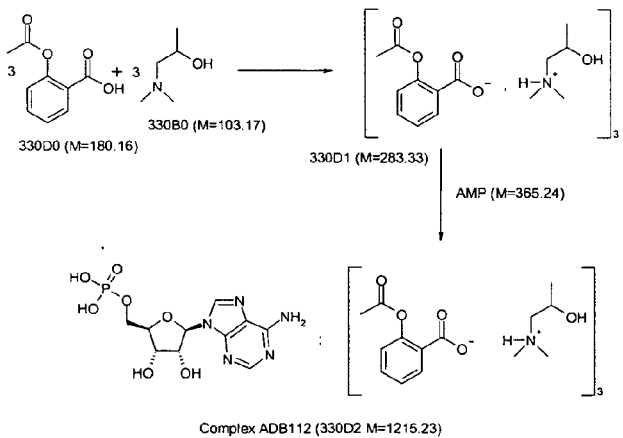
330D0= acetyl salicylic acid Figure 3d NMR 1H of Adb-012
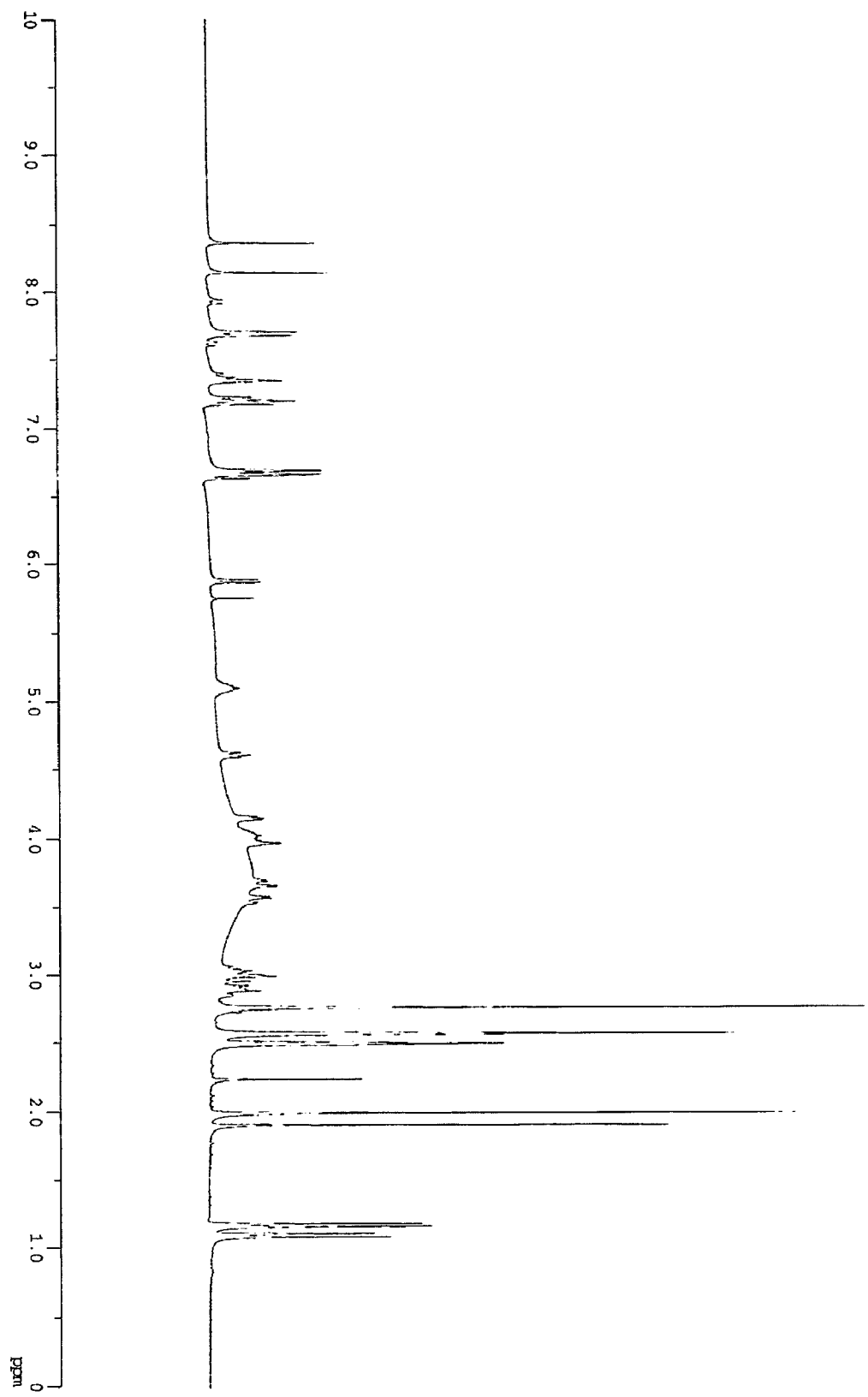

Figure 3e NMR 1H of Adb-112 (DMSO)
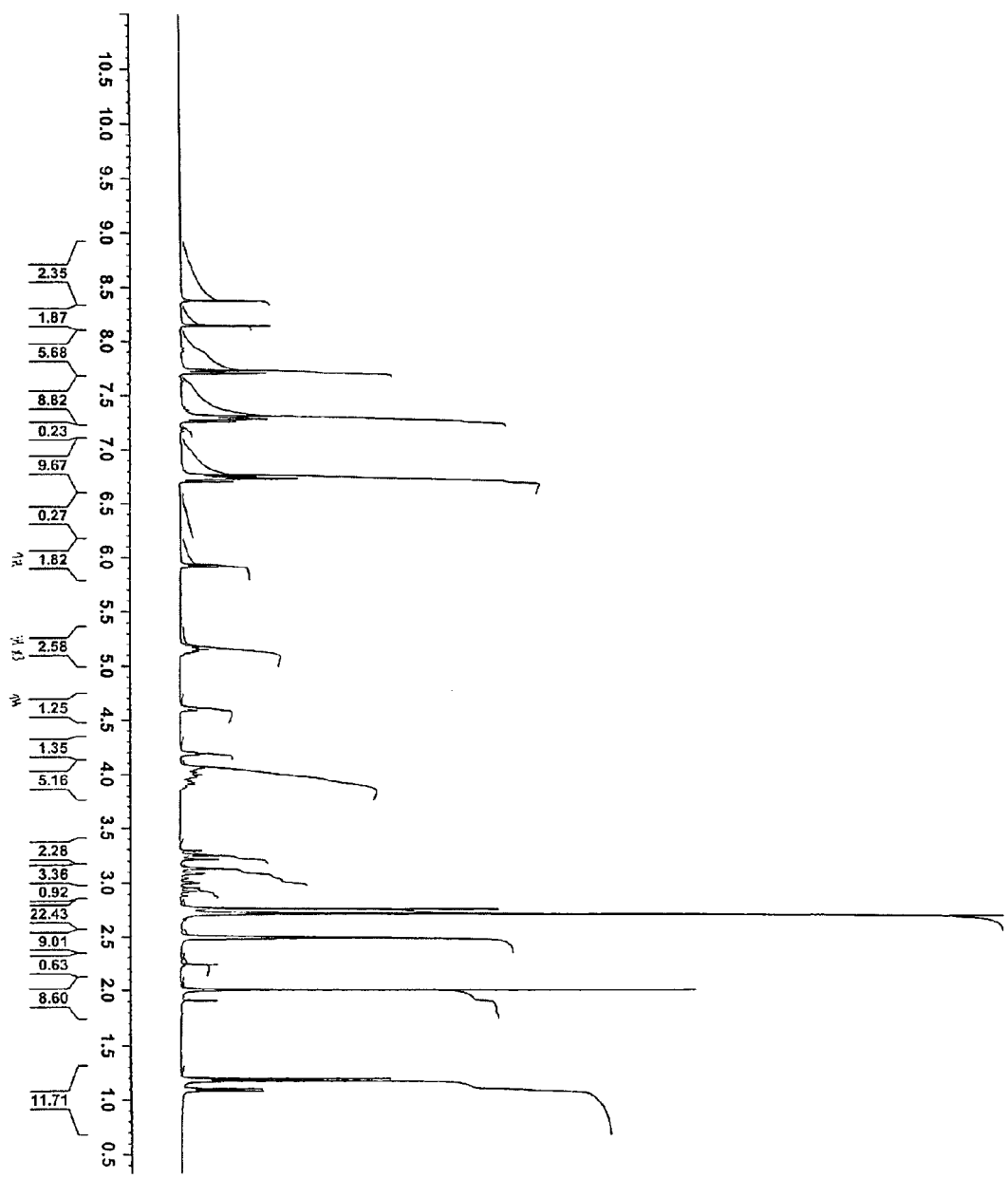

Figure 4. Infra-Red spectrum of ADB011:
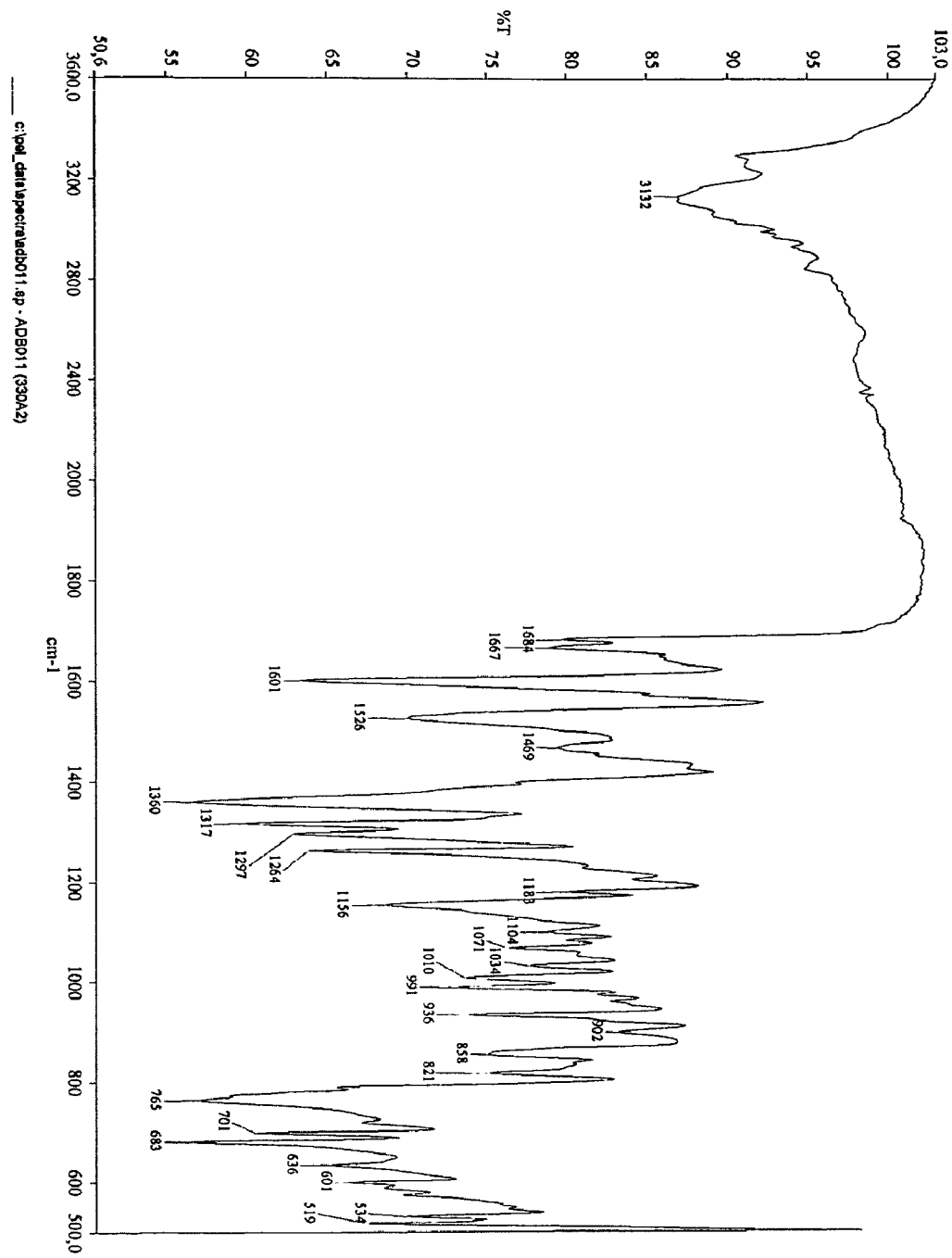

Figure 5. Infra-Red spectrum of ADB111:
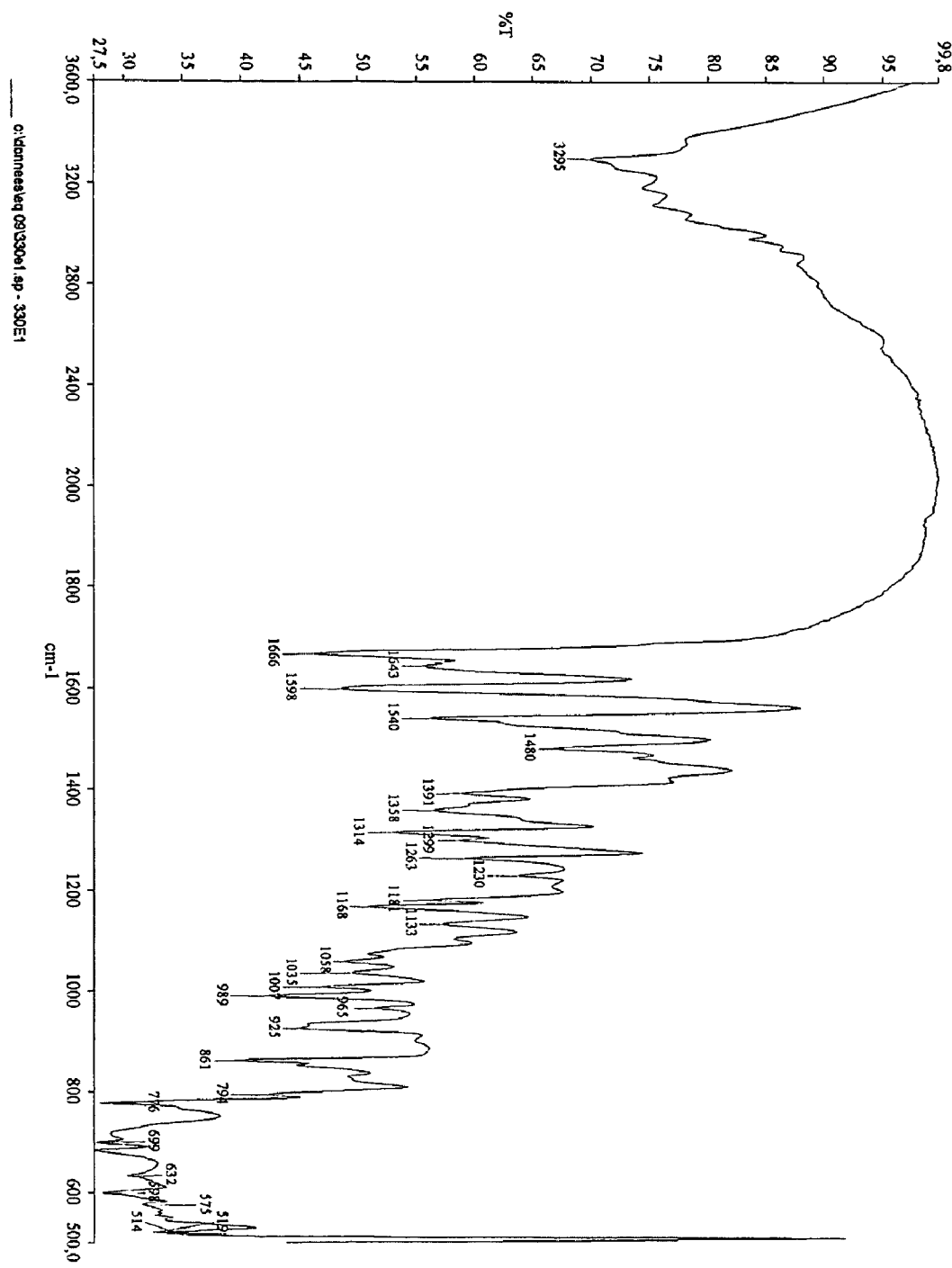

Figure 6. Infra-Red spectrum of ADB311:
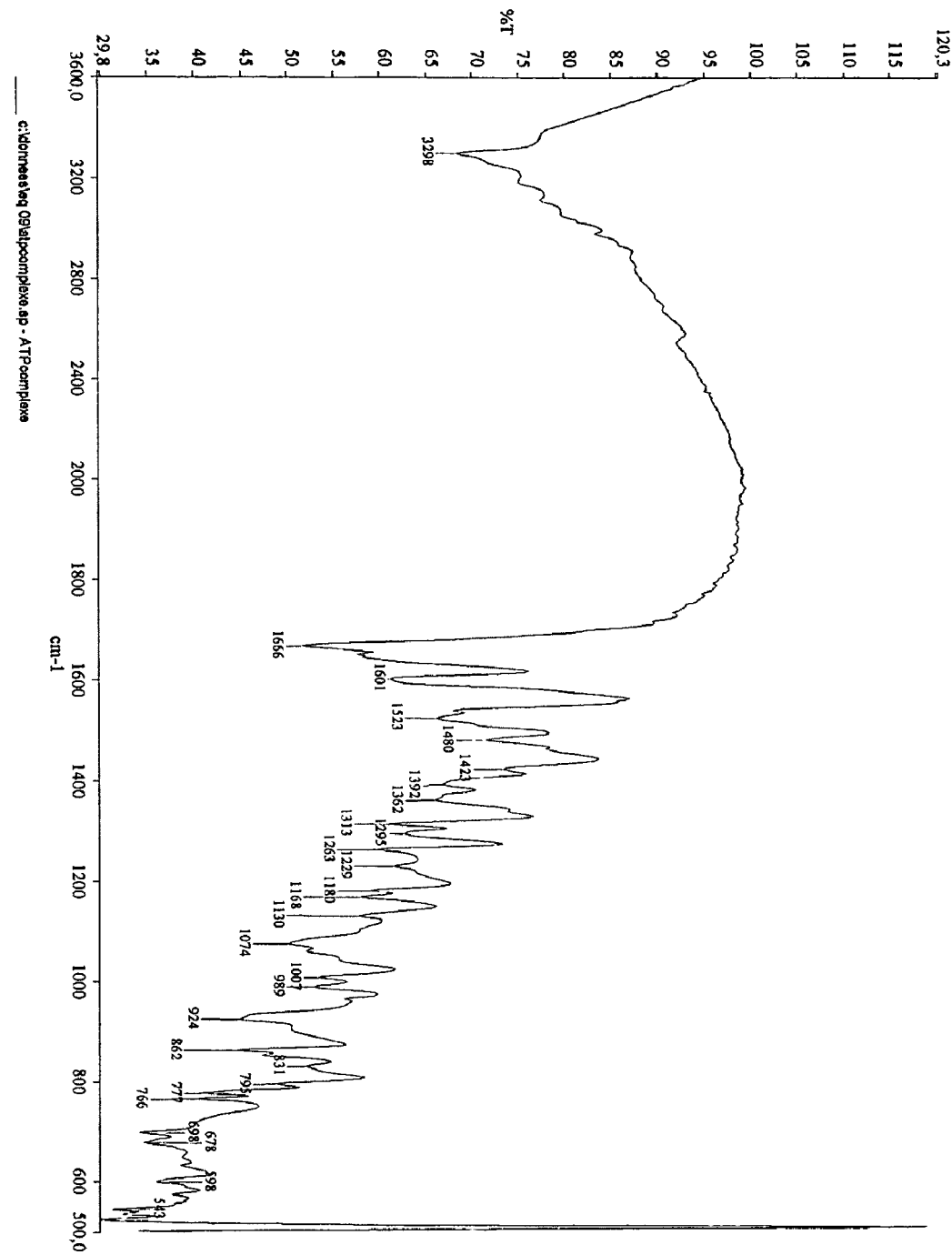

Figure 7. Infra-Red spectrum of the difference between the two spectra, that of ADB011 and that of the mixture adenosine/salt (330A1): 1/3.
Conclusion: Between wave number 2800cm$^{-1}$ and 1800cm$^{-1}$, no difference is shown between ADB011 and its original components. Between 3600-3200cm$^{-1}$, and 1700-500cm$^{-1}$, curves are very different.
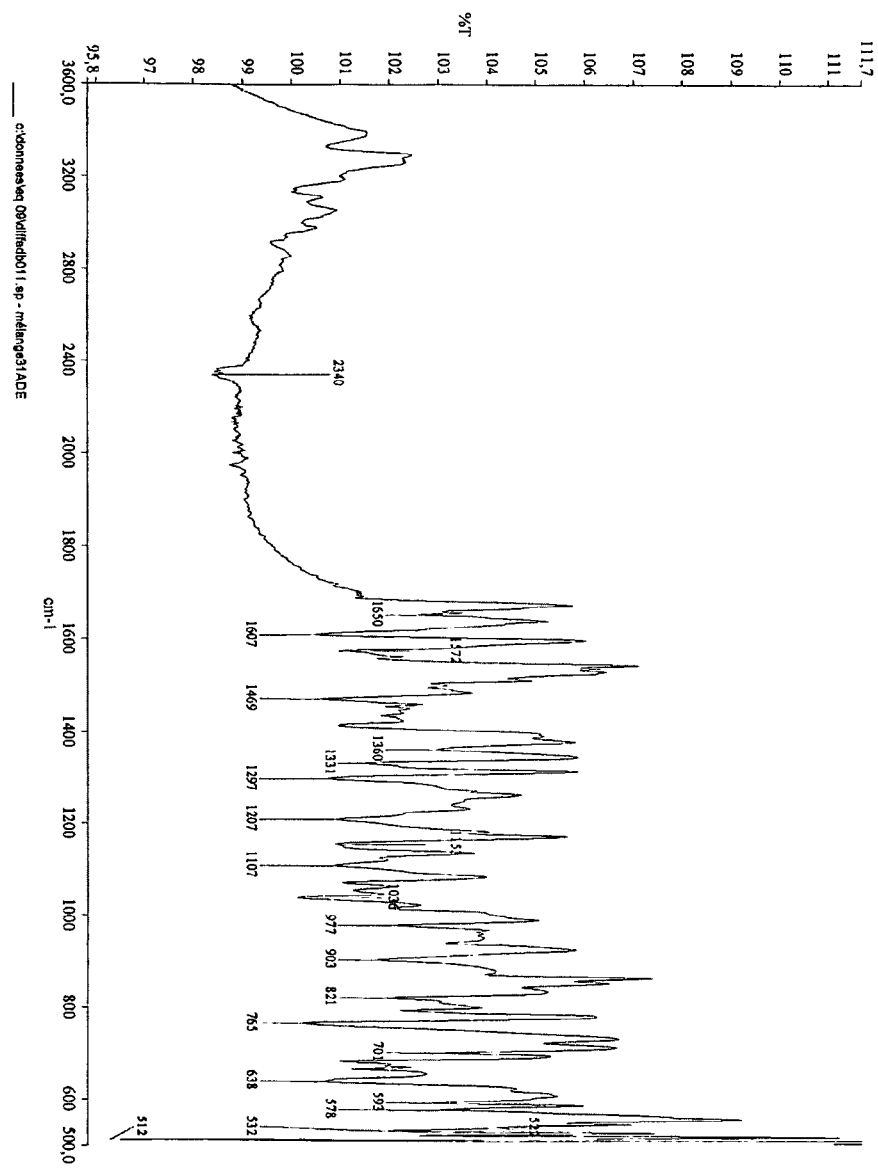

Figure 8. Infra-Red spectrum of the difference between the two spectra: ADB111 (complex AMP with salt) and mixture AMP/salt (330A1): 1/3.
Conclusion: Between wave number 2800cm$^{-1}$ and 1800cm$^{-1}$, no difference is shown between ADB111 and its original components. Between 3600-3200cm$^{-1}$, and 1700-500cm$^{-1}$, curves are very different.
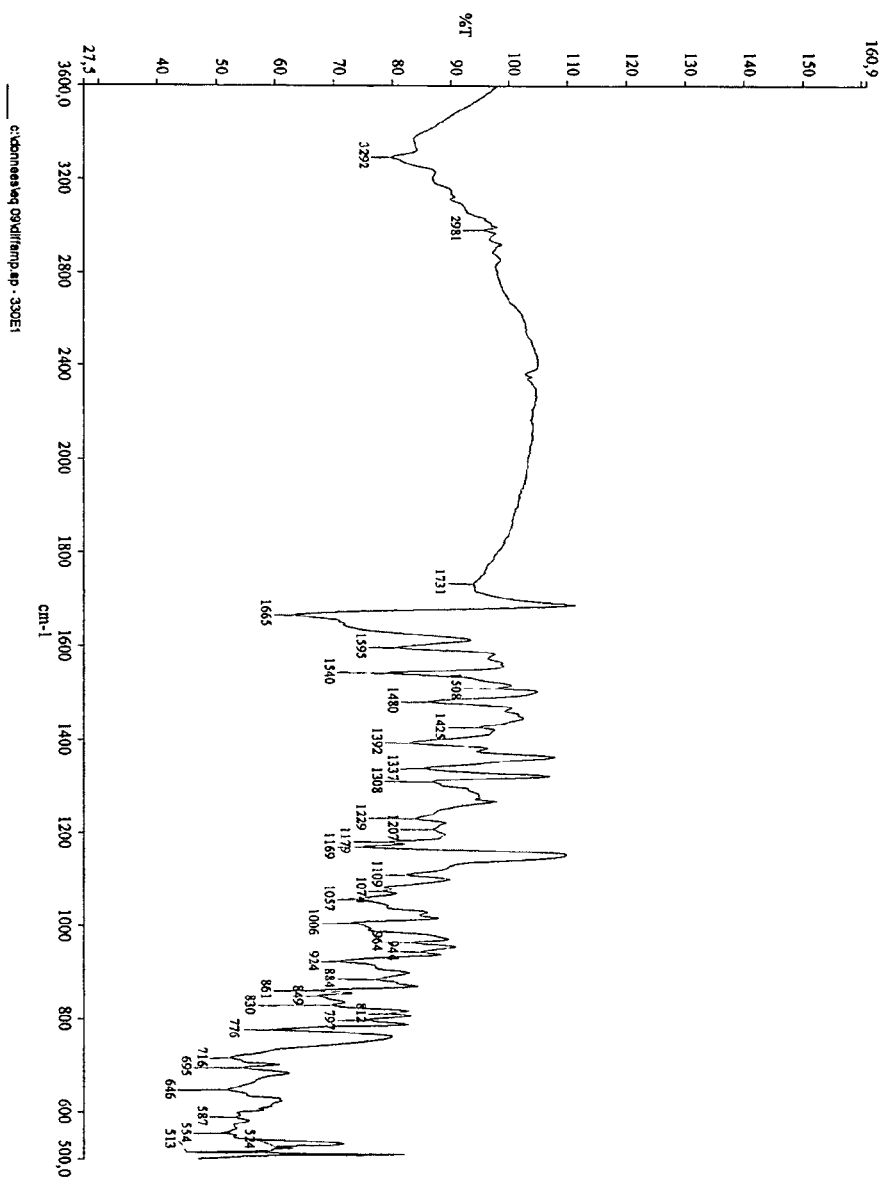

Figure 9. Infra-Red spectrum of the difference between the two spectra: ADB311 (complex ATP with salt) and mixture ATP/salt(330A1): 1/3.
Conclusion: Between wave number 2800cm$^{-1}$ and 1800cm$^{-1}$, no difference is shown between ADB311 and its original components. Between 3600-3200cm$^{-1}$, and 1700-500cm$^{-1}$, curves are very different.
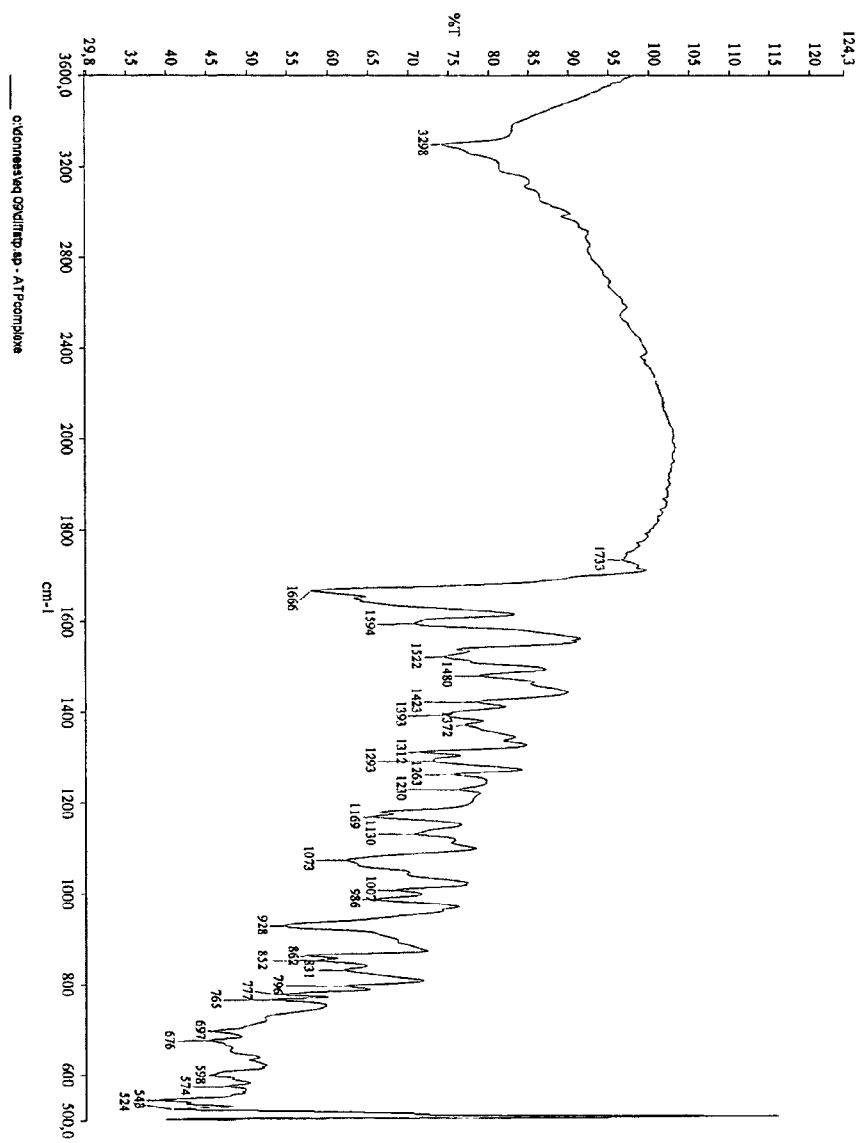

Figure 10. Adb011 : Effects by the oral route on blood pressure
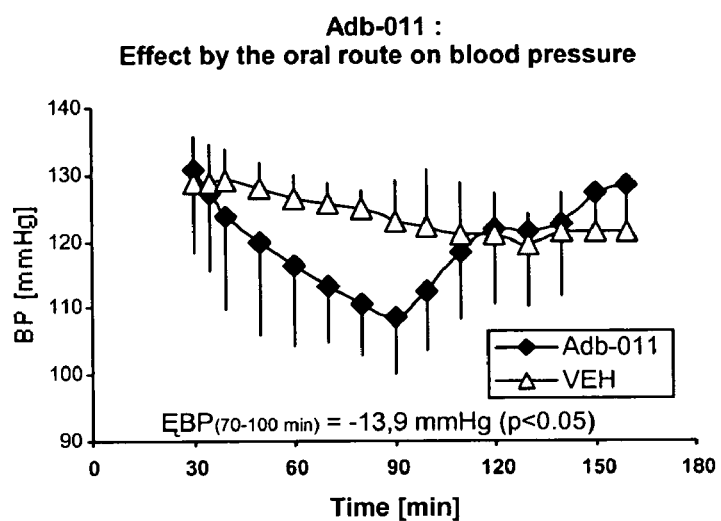
*Blood pressure lowering action of oral Adb-011 (p value was calculated by ANOVA multiple measurement analysis followed by Bonferroni-Dunn test).*

Figure 11. Effects of Adb011 (complex of adenosine with salt) IV-10mg bolus administration on systemic arterial blood pressure

The lowering effect of Adb011 is still strong after two hours.
One should compare this to the less than one minute lowering arterial pressure effect of adenosine after a 6mg to 12mg bolus injection in animals and humans (Adenocor, Adenocard monographs).

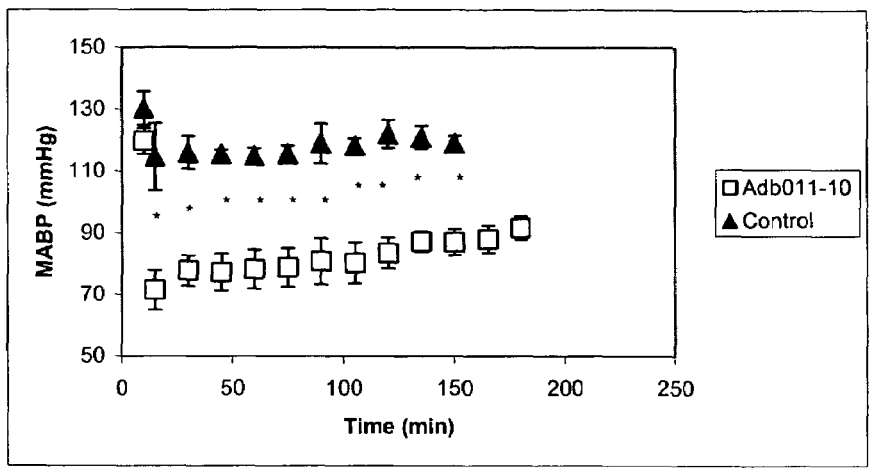

MAPB (Mean Arterial Blood Pressure) Blood pressure lowering action of oral Adb011-10mg/kg. (p value was calculated by t-test) ), * $p<0.05$ Adb011 vs Control

Figure 12

Chronic Adb-011 administration to hypoxic rats with established pulmonary artery hypertension

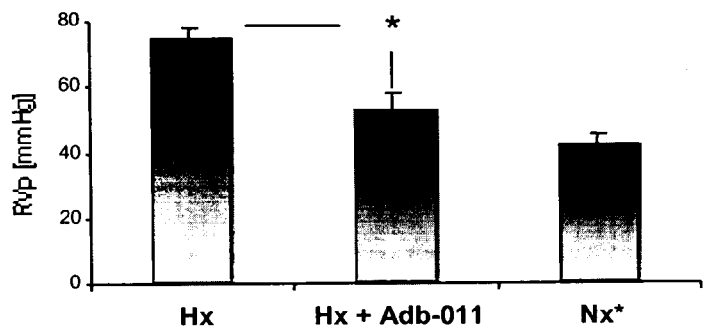

Effect of orally given Adb-011 (50 mg/kg twice-a-day for 14 days) on rigth ventricular pressure of hypoxic rats. Values are given as mean ±SEM. * indicates $p < 0.05$ (Mann Whitney U test).Hx indicates hypoxic rats. Normoxic(Nx) values were from data in Rpt Adb-011 2004/1.

Acute Adb-011 administration to hypoxic rats with established pulmonary artery hypertension

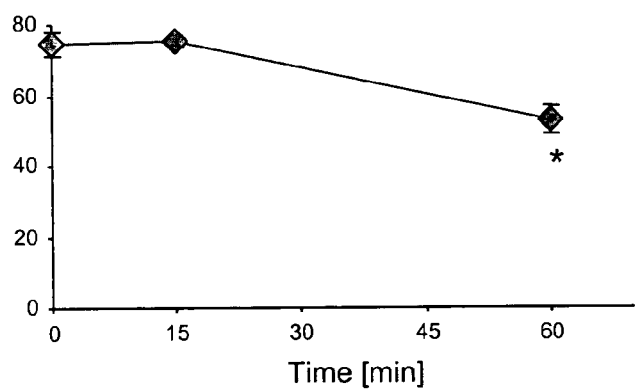

Effect of a single oral dose of Adb-011 (50 mg/kg) on rigth ventricular pressure of hypoxic rats. Values are given as mean ±SEM. * indicates $p < 0.05$ (Mann Whitney U test).

Figure 13. Adb-111 : Effects by the oral route on systemic arterial pressure in rats. Comparison with oral Adenosine monophosphate
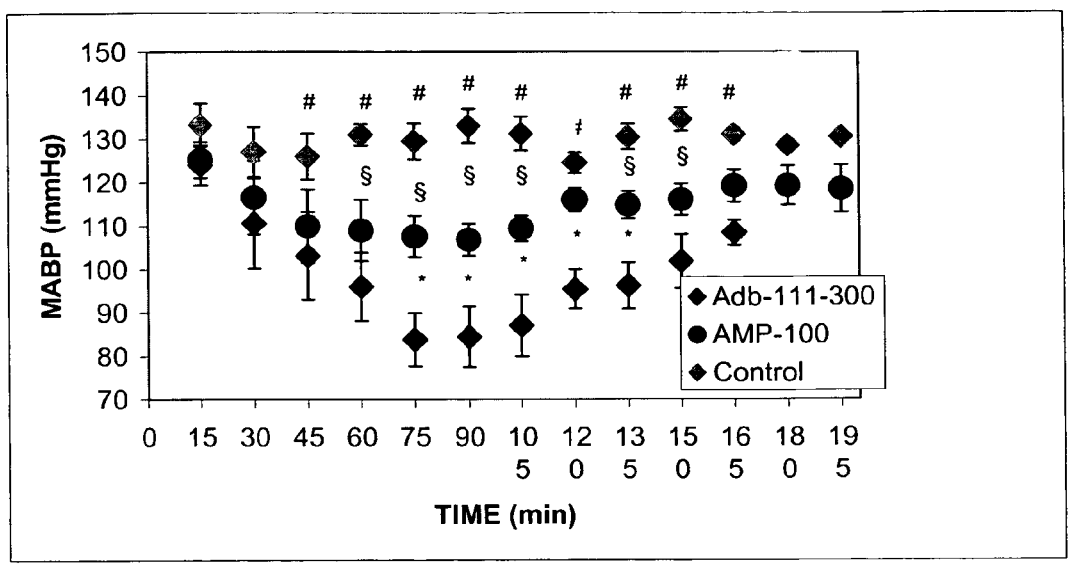
MAPB (Mean Arterial Blood Pressure) Blood pressure lowering action of oral Adb111-300mg/kg. (p value was calculated by t-test) ), * p<0.05 Adb111-300 vs AMP-100; § p<0.05 AMP-100 vs control; # p<0.05 Adb111-300 vs control Figure 14. Effects of orally and intravenously given 330A1 on systemic arterial blood pressure
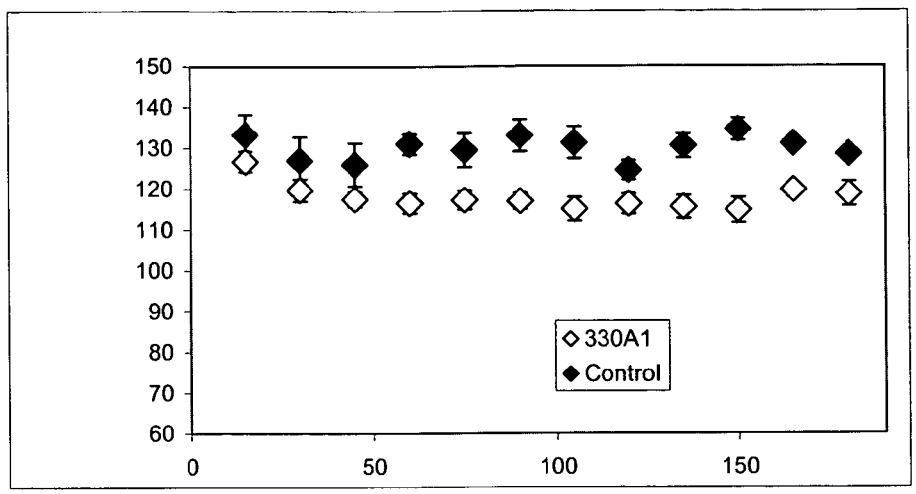
MAPB (Mean Arterial Blood Pressure) Blood pressure lowering action of oral 330A1-50mg/kg
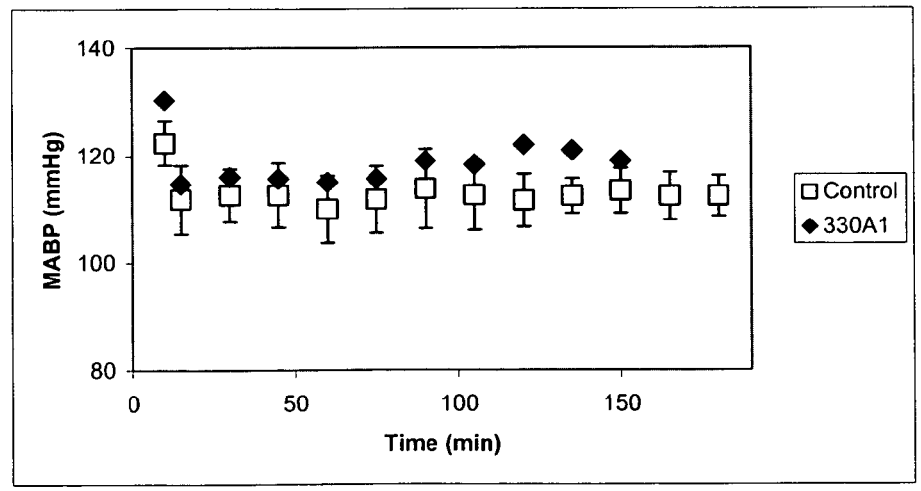
MAPB (Mean Arterial Blood Pressure) Blood pressure lowering action of IV 330A1-10mg/kg

STABLE AND ACTIVE COMPLEXES OF ADENOSINE AND ADENOSINE PHOSPHATES WITH AMINOALCOHOLS FOR THE TREATMENT OF PULMONARY ARTERY HYPERTENSION, CARDIAC FAILURE AND OTHER DISEASES

BACKGROUND OF THE INVENTION

1. Field of the Invention

The present invention relates to stable and active complexes of adenosine, adenosine monophosphate and adenosine triphosphate with aminoalcohols, alkylamino-alkanols, dialkylamino-alkanols, and their salts for treating cardiovascular and neurological and other diseases including, but not limited to, pulmonary artery hypertension, cardiac failure and cerebral vasospasm.

2. Description of the Prior Art

1. Adenosine

Adenosine is a ubiquitous purine that is a modulator of numerous physiological activities, particularly within the cardiovascular and nervous systems. Adenosine has a variety of extracellular and intracellular effects. The effects of adenosine appear to be mediated by specific cell surface receptor proteins (A1, A2a, A2b, and A3). Adenosine modulates diverse physiological functions including, arterial vasodilation, reduction of cardiac rate, down regulation of several brain activities, inhibition of acute inflammation, stimulation of gluconeogenesis, and inhibition of lipolysis. Adenylate cyclase mediates many of adenosine's effects, e.g., the opening of potassium channels and the reduction of flux through calcium channels.

1.1 Adenosine is a potent arterial vasodilator.

Adenosine constantly modulates vascular tone, significantly under ischemic conditions, thus contributing to the protection of a large number of tissues (heart, brain, liver, kidney, stomach, etc.). Currently, adenosine vasodilating properties are used for ischemic heart disease diagnosis (e.g., as an adjunct to thallium-201 myocardial perfusion scintigraphy in patients unable to exercise adequately) and occasionally for cardioprotection during revascularization procedures.

Acting via A2 receptors adenosine increases cyclic AMP which promotes vasodilatation by both decreasing intracellular calcium and directly inhibiting myosin light chain kinase phosphorylation.

Adenosine has a preferential vasodilator effect on the pulmonary circulation in human. Morgan J M—*Adenosine as a vasodilator in primary pulmonary hypertension. Circulation.* 1991 September; 84(3):1145-9. This effect is confined to the pulmonary arterial tissues for dosages in the 50 μg/kg/mn range given in perfusion for 15 minutes. Fullerton D A—*Adenosine effectively controls pulmonary hypertension after cardiac operations—Ann Thorac Surg.* 1996 April; 61(4):1118-23. At dosages of 140 μg/kg/mn for 6 mn (Adenoscan prescribing information) a systemic vasodilating effect is observed and hypotension can be seen in 2% of patients. Due to its very short half-life, less than 5 seconds, usage of adenosine is currently limited to IV acute testing in order to determine those patients who may respond to calcium channel blockers or other vasodilating therapies prescribed in pulmonary artery hypertension.

Adenosine induces collateral circulation via inducing growth factors and triggering ischemic preconditioning, both of which induce ischemic tolerance in advance. Adenosine is also known to reduce the release of noradrenaline, production of endothelin, and attenuate the activation of renin-angiotensin system, all of which are believed to cause cardiac hypertrophy and remodelling. Exogenous adenosine is further known to reduce the severity of ischemia and reperfusion injury. Finally, adenosine is reported to counteract neurohumoral factors, i.e., cytokine systems, known to be related to the pathophysiology of cardiac failure. Kitakaze M, Hori M—*Adenosine therapy: a new approach to chronic heart failure. Expert Opin Investig Drugs* 2000 November; 9(11):2519-35.

Intra-arterial (133)Xe cerebral blood flow (CBF) measurements suggest that intracarotid adenosine, in a dose that lacks significant systemic side effects, profoundly increases CBF, whereas nitroprusside has no effect. Joshi S et al—*In nonhuman primates intracarotid adenosine, but not sodium nitroprusside, increases cerebral blood flow. Anesth Analg.* 2002 February; 94(2): 393-9.

In the heart, adenosine has been shown to suppress pacemaker activity and slow atrio-ventricular conduction. It is currently used by intravenous bolus administration to treat supraventricular tachycardia.

1.2 Adenosine is a neuromediator.

In most brain areas, high extracellular adenosine concentrations, through A1 and A2 adenosine receptors, decrease neuronal activity. See Dunwiddie T V, Masino S A., *Neuroscience* 2001, 107(4):653-63. See also, *The role and regulation of adenosine in the central nervous system. Annu. Rev. Neurosci.* 2001; 24:31-55.

Adenosine is also thought to play a key role in the induction of sleep. Investigations into the relationship between adenosine and sleep surged following the discovery that caffeine's stimulating characteristics stem from its ability to prevent adenosine from binding to cells and launching distinct actions. Now a large body of work has revealed the details of how, under normal circumstances, adenosine promotes sleep. Many studies in animals have shown that blocking adenosine's actions in the brain increases alertness, while injections of adenosine or similar compounds induce apparently normal sleep. See Porkka-Heiskanen T., et al., *Adenosine: A mediator of the sleep-inducing effects of prolonged wakefulness.* Science 276 (May 23):1265, 1997.

Adenosine also participates in many local regulatory mechanisms, such as those occurring in synapses, in the central nervous system (CNS) and at neuroeffector junctions in the peripheral nervous system. In the CNS, adenosine is known to inhibit the release of a variety of neurotransmitters, such as noradrenaline, dopamine, serotonin, glutamate and GABA, to depress neurotransmission, to reduce neuronal firing, to induce spinal analgesia, and to possess anxiolytic properties.

Adenosine can also function as an inhibitory modulator of seizure activity, of particular importance in epilepsy and convulsions of the alcohol withdrawal syndrome. For review, see Ph. De Witte, E. Pinto, M Ansseau and P. Verbanck. *Alcohol and withdrawal: from animal research to clinical issues, Neuroscience & Biobehavioral Reviews,* 2003;27:189-197. This likely represents an adaptive response to seizure severity induced by repeated episodes of withdrawal.

The identification of adenosine as a transactivator or the Trk tyrosine kinase receptor suggests that it can replace neurotrophins as a potential treatment for a wide range of neurological disorders, including Alzheimer disease, cerebral ischemia, hyperalgesia, and Parkinson's disease. See Lee F S, Rajagopal R, Chao M V *Distinctive features of Trk neurotrophin receptor transactivation by G protein-coupled receptors. Cytokine Growth Factor Rev.* 2002 February 13(1):11-7. Indeed, adenosine activates the Trk receptor tyrosine kinase and mediates neuronal cell survival in the absence of neurotrophins. Adenosine also offsets impaired cholinergic signalling. The regulation of the cholinergic calcium signalling in astroglial cells is thought to play a crucial role in the pathogenesis of Alzheimer's disease. Various study results suggest that impaired cholinergic signalling, the cardinal symptom of Alzheimer's disease, can be reinforced at the second messenger level by an alternative intracellular Ca(2+) mobilizing path, which can be brought into play by the concomitant activation of A1 purinoceptors. See Ferroni S, Marchini C, Ogata T. Schubert P., *J Neurosci Res.* 2002 June 1;68(5):615-21, *Recovery of deficient cholinergic calcium signalling by adenosine in cultured rat cortical astrocytes.* Therefore, it is thought that adenosine can stop and prevent neurons from calcium dysregulation.

1.3 Adenosine has anti-inflammatory properties.

Adenosine signalling strongly affects inflammatory cell function. (Ohta, A. & Sitkovsky, M *Role of G-protein-coupled receptors in downregulation of inflammation and protection from tissue damage. Nature* 414, 916-920 (2001)) thus resulting in:

Inhibition of leucocytes migration and free radical production. Cronstein B N. *Adenosine, an endogenous anti-inflammatory agent, J Appl Physiol* 1994 January; 76(1): 5-13.

Down-regulation of pro-inflammatory cytokines such as TNF-alpha, IL-6, IFN-gamma, IL-12, and the up-regulation of the anti-inflammatory cytokine IL-10. Zdenek Zidek .*Adenosine cyclic AMP pathways and cytokine expression—Review—European Cytokine Network.* Vol. 10, Issue 3, September 1999: 319-28.

A2 receptor stimulation also inhibits NFkappaB activity, whereas activation of other adenosine receptors have no effect (activation of NFkappaB induces gene programs leading to transcription of factors that promote inflammation, such as leukocyte adhesion molecules, cytokines, and chemokines).

Despite its role in multiple biological functions and pharmacological processes, the very short plasmatic half-life of adenosine (less than 5 sec.) restricts its therapeutic use to massive bolus injections by the intravenous route for treating supraventricular tachycardia with the risk of serious A1 related adverse-effects such as chest-pain, AV block, and bronchoconstriction.

2. AMP

The purine nucleotide AMP is a natural "adenosine precursor" which ultimately converts into adenosine by ecto-5'-nucleotidase on the extra-cellular surface of all cells. Ecto-5'-nucleotidase is a ubiquitous wide spread enzyme that hydrolyzes a variety of nucleotides, but has greatest affinity for AMP that it efficiently converts to adenosine. The vasodilating effects of AMP are mentioned in the *Monographs of Commercialized AMP Products Cardiomone and Adenyl.*

3. ATP

ATP is a naturally occurring nucleotide which is present in every cell. Extracellular ATP appears to be involved in the regulation of a variety of biological processes via P2 receptors divided into P2X ligand-gated ion channel and P2Y G-protein-coupled receptors families.

3.1 ATP potentiates cytostatic agents.

In in vitro and in vivo animal studies, ATP has been shown to inhibit the growth of several solid carcinoma tumours (colon, pancreas, esophagus) and of several cancer cell lines (prostate, breast, melanoma, myeloid cells). See Agteresch H J & al, *Adenosine Triphosphate. Established and potential clinical applications. Drugs* 1999 August; 58(2):211-232. The underlying predominant mechanism is not clear but increased membrane permeability (not observed in untransformed cells) seems predominant. Potentiation effects of cytostatic agents were also observed in several in vitro and animal studies (melanoma, ovarian carcinoma) and some human studies (myeloid leukaemia, glioma).

ATP infusion in patients with advanced cancer is feasible but is limited by dyspnoea and chest tightness. A Phase II trial in patients with non-small cell lung cancer showed that it reduces or inhibits weight loss. See Haskell C M & al., *Phase I trial of extracellular ATP in patients with advanced cancer. Med Pediatr Oncol* 1996; 27(3):165-73. This effect has also been observed in mice with human pancreatic carcinoma.

Cachexia is caused by elevated lipolysis, protein breakdown and gluconeogenesis. It is also correlated with lower ATP levels. It was suggested that the administration of extracellular ATP inhibits Cori cycle (i.e. the gluconeogenesis from lactate followed by reconversion of glucose to lactate in peripheral tissue), activity which is a potential means of inhibiting weight loss.

3.2 ATP is the universal source of cell energy.

ATP is depleted during exercise, in chronic fatigue syndrome and in heart failure. See Steele D S, Duke A M. *Metabolic factors contributing to altered Ca2+ regulation in skeletal muscle fatigue* Acta Physiol Scand. 2003 September; 179(1):39-48/Harmer A R & al-*Skeletal muscle metabolic and ionic adaptations during intense exercise following sprint training in humans* J Appl Physiol. 2000 November; 89(5):1793-803/Forsyth L M. *Therapeutic effects of oral NADH on the symptoms of patients with chronic fatigue syndrome.* Ann Allergy Asthma Immunol. 1999 February; 82(2): 185-91/Ventura-Clapier R. *Metabolic myopathy in heart failure.* News Physiol Sci. 2002 October; 17:191-6/*Energy metabolism in heart failure.* Physiol. 2004 February 15;555 (Pt 1):1-13. Epub 2003 Dec. 05.

3.3 ATP is a potent vasodilating agent.

ATP exerts its vasodilating effects mainly through P2Y receptors and ATP-sensitive potassium channel openers. Van Aken H et al-*Haemodynamic and cerebral effects of ATP-induced hypotension. Br J Anaesth.* 1984 December; 56(12): 1409-16.

Despite possessing numerous and very important physiological and pharmacological activities, adenosine and adenosine triphosphate (ATP) have both a very short plasma half-life (less than 5 seconds) and therefore cannot be used orally. Although having a longer half life, adenosine monophosphate (AMP) has a poor gastrointestinal bioavailability which restricts its medical applications. Further, when administered intravenously, the effects of adenosine and ATP are limited in duration (e.g. less than one minute after adenosine bolus injection). Thus, there is a need for improved compositions and methods which take advantage of the pharmacological effects of adenosine and adenosine phosphates while having improved stability when administered orally (as well as intravenously).

Given that adenosine and adenosine phosphates possess numerous physiological and pharmacological activities significant research has been devoted in the pursuit of harnessing their pharmacological effects in therapeutic compositions and methods. For example, U.S. Pat. No. 3,993,639 (the '639 patent) describes heptaminol adenosine-5'-monophosphate. This compound has interesting properties in the cardiovascular domain, particularly in the treatment of venous vascular insufficiencies (phlebology). However the '639 patent document does not teach nor suggest the formation of complexes between adenosine and tertiary amines such as dialkylaminoalkanols nor pharmaceutical compositions between adenosine monophosphate and tertiary amines as dialkylaminoalkanols nor that primary amine heptaminol might improve adenosine-5'-monophosphate bioavailability. Thus, no properties of such complexes, e.g. enhanced capacity to cross the gastrointestinal barrier, are described or suggested.

The present invention provides compositions and method which permit the oral use of adenosine and adenosine phosphates for cardiovascular applications such as pulmonary artery hypertension, cardiac failure and other diseases. The invention also enhances AMP gastrointestinal bioavailability and efficacy. The invention further permits prolonged activity of those substances when administered intravenously. In addition, the invention contemplates method of treating several human (as well as animal) cardiovascular and neurological medical conditions that could be improved by an effective amount of adenosine, ATP or AMP combined with dialkylaminoalcohols and their salts.

SUMMARY OF THE INVENTION

One embodiment of the invention includes compositions comprising complexes of adenosine or an adenosine phosphate with a dialkylamino-alkanol.

Another embodiment of the invention includes compositions comprising complexes of adenosine or an adenosine phosphate with a dialkylamino-alkanol having the formula:

where R1 and R2 are lower alkyl and n is an integer of 2 to 16.

Another embodiment of the invention is a composition comprising complexes of adenosine or an adenosine phosphate with dimethylamino isopropanol.

An additional embodiment of the invention is a composition comprising complexes of either adenosine or an adenosine phosphate with any one of dimethylamino ethanol, diethylamino ethanol, diethylamino isopropanol, methylethylamino ethanol, dimethylamino propanol, dimethylaminoisopropanol, dimethylaminobutanol, dibutylaminoethanol, dipropyl aminoethanol, or diisopropylamino ethanol.

Embodiments of the present invention also contemplate a composition comprising a mole ratio of either adenosine or an adenosine phosphate to dimethylaminoalkanol of about 1:1 to 1:10.

The present invention further contemplates a pharmacologically active salt of complexes of adenosine or an adenosine phosphate with a dialkylamino-alkanol.

One embodiment of the instant invention contemplates methods of treating cardiovascular and cerebrovascular diseases, systemic arterial hypertension, cardiac failure, ischemic heart disease, peripheral arterial diseases, cerebral vasospasm, pulmonary arterial hypertension, inflammatory diseases, thrombosis, pathology of sleep, neurodegenerative disease, malignant tumor growth inhibition and enhancement of cancer chemotherapy using complexes of adenosine or adenosine phosphates by oral or parenteral routes.

Another embodiment of the instant invention comprises novel compositions which allow adenosine and adenosine phosphates to cross the gastrointestinal barrier after oral administration.

A further embodiment of the invention prolongs adenosine and adenosine phosphate activity and efficacy when administered intravenously.

Additional embodiments of the present invention contemplate methods of crossing the blood brain barrier by incorporating adenosine and adenosine phosphate complexes into nanoparticules or liposome systems.

Embodiments of the present invention also contemplate an adenosine or adenosine phosphates complexes with aminoalkanol, or alkylamino-alkanol or dialkylamino-alkanol for use in methods of treating neurological diseases such as the pathology of sleep, psychological disorders, neurodegenerative diseases and more particularly Alzheimer disease, pain, dependence withdrawal and epilepsy.

Embodiments of the present invention also contemplate an ATP complex with amino-alkanol, or alkylamino-alkanol or dialkylamino-alkanol for use in methods of treating malignant tumor growth, enhancement of cancer chemotherapy, weight loss, and fatigue syndrome.

Embodiments of the present invention provide methods of sustained release delivery of adenosine, ATP and AMP into the circulation when those substances are combined with a dialkylamino-alkanol and are administered via the IV route.

These and other embodiments of the present invention, which will become better understood during the course of the following detailed description, have been achieved by the inventor's discovery of stable complexes produced by the reaction of adenosine and/or adenosine phosphates with certain amino alcohols. These complexes have many therapeutic properties which are further described throughout the Detailed Description below.

BRIEF DESCRIPTION OF THE FIGURES AND DRAWINGS

FIG. 1 shows the synthesis of compound 330A1 and of compound 330A2 currently named Adb011 (adenosine with 4-acetamidobenzoic acid and dimethylaminopropanol).

FIG. 2 shows the synthesis of adenosine triphosphate with 4-acetamidobenzoic acid (p-aminobenzoic acid derivative) and dimethylaminopropanol (Adb311) and that of adenosine monophosphate with 4-acetamidobenzoic acid and dimethylaminopropanol (Adb111).

FIG. 3a shows the synthesis of adenosine with adipic acid and dimethylaminoisopropanol (Adb013).

FIGS. 3b and 3c show the synthetic pathways of adenosine with acetyl salicylic acid and dimethylaminoisopropanol (Adb-012) and that of adenosine monophosphate with acetyl salicylic acid and dimethylaminoisopropanol (Ad-112).

FIG. 3d shows an NMR of compounds Adb-012.

FIG. 3e shows an NMR of compounds Adb-112.

FIG. 4 to 9 are the infrared curves for 3 compounds compared to their components. The curves illustrate the novelty of the complexes since those latter have a different infrared spectrum and drawing.

FIG. 10 shows mean values of blood pressure in 5 rats receiving 50 mg/kg Adb011 and 5 rats receiving vehicle (control group).

FIG. 11 shows mean values of blood pressure in 4 rats receiving 10 mg/kg Adb011 intravenously and 3 rats receiving vehicle (control group).

FIGS. 12 show the effects of Adb011 given orally in rats with acute and chronic pulmonary artery hypertension.

FIGS. 13 show the effect on blood pressure of Adb111 and AMP given orally in normal rats at comparable dosages.

FIGS. 14 shows the effect on blood pressure of compound 330A1 (salt of the complexes) given either orally or IV in normal rats.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implicated in other compositions and methods, and that any such variation would be within such modifications that do not part from the scope of the present invention. Before explaining the disclosed embodiments of the present invention in detail, it is to be understood that the invention is not limited in its application to the details of any particular embodiment shown, since of course the invention is capable of other embodiments. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

The present invention relates to novel adenosine, adenosine monophosphate and adenosine triphosphate complexes. The inventors of the instant invention have surprisingly discovered complexes of adenosine and adenosine phosphates with amino-alcohols that are stable when administered orally or intravenously. These complexes are useful in the treatment of pulmonary artery hypertension, cardiac failure and other diseases due to their enhanced stability and/or half life. The present invention renders it possible to use adenosine and ATP via the oral route, improves AMP bioavailability when used orally, and provides methods for sustained release delivery of adenosine, ATP and AMP into the blood stream.

Previously, complexes of inosine and amino-alcohols have been produced. For example, U.S. Pat. No. 3,646,007 (the '007 patent) describes complexes of inosine and dialkylaminoalcohols of the formula $R_1R_2N(C_nH_{2n})OH$, where $R_1$ and $R_2$ are lower alkyl and n is an integer of 2 to 16 (methyl to butyl), where the preferred aminoalcohol compound is dimethylaminoisopropanol. These complexes are described as having pharmacological activities including the ability to restore deteriorated learning and memory behavior. They are further said to reduce senility and aging characteristics, combat viral diseases, and aid in the treatment of neuroatrophic diseases. The instant invention is neither taught nor suggested by the '007 patent. Inosine is not adenosine. Inosine is not a mediator as adenosine is. Further, the stability of inosine, when orally administered, is not an issue, whereas with adenosine it is. The '007 document never describes nor suggests complexes of adenosine nor adenosine phosphates with aminoalcohols. This document does not teach or suggest that a complex made with a tertiary amine, such as dialkylaminoalcohols, may enhance the stability of inosine complexes, let alone complexes of adenosine. Thus, one skilled in the art will not consider such complexes for enhancing the stability of adenosine, since the '007 patent contains no teaching regarding adenosine or stable complexes of adenosine, or adenosine phosphates, with dialkylaminoalcohols.

The complexes of the instant invention are formed with either adenosine, adenosine monophosphate or adenosine triphosphate with a dialkylamino-alkanol of the formula:

where R1 and R2 are lower alkyl and/or H and n is an integer of 2 to 16. A preferred aminoalcohol is dimethylaminoisopropanol (R1 and R2=methyl). These complexes can be used in the form of free base or in the form of their salts with pharmacologically acceptable acids. Typical adenosine, AMP or ATP complexes include the complexes dimethylamino ethanol, dimethylaminoisopropanol, diethylaminoethanol, diethylaminoisopropanol, methylethylamino ethanol, dimethylaminopropanol, dimethylaminobutanol, dibutylaminoethanol, dipropylaminoethanol, and diisopropylaminoethanol.

Acceptable acids for forming salts include any pharmacologically acceptable acids or their derivatives including, but not limited to, hydrochloric acid, sulphuric acid, phosphoric acid, acetyl salicylic acid, d-tartratic acid, maleic acid, fumaric acid, succinic acid, citric acid, trans cinnamic acid, salicylic acid, 5-amino-salicilyc acid, sulfasalazine, adipic acid, methane sulfonic acid, acetic acid, hyaluronic acid, and p-aminobenzoic acid. Other acids include arylacetic acid derivatives such as diclofenac, sulindac. Acids can be also be selected from arylpropionic acid derivatives such as: flurbiprofen, ibuprofen, ketoprofen, and naproxen.

Most of the salts with amines are hygroscopic. However, the p-aminobenzoic acid salt and more specifically the 4-acetamidobenzoic acid of the adenosine-dimethylamino isopropanol complex (or AMP or ATP-dimethylamino isopropanol complexes) is a solid and is the presently preferred salt. It is prepared by mixing the aminoalcohol and the acid mole for mole and then heating slightly. The salt thus formed is then dry mixed with adenosine (or AMP, or ATP) in a mole ratio of, for example, either 1:1 or 3:1 (salt to adenosine or AMP or ATP). The complex is then formed, for example, by dissolving in water and can be recovered there from if desired by evaporation. The preferred ratio of adenosine (or ATP) to aminoalcohol is 1:3.

The adenosine complexes of the instant invention have pharmacological activities including the ability to lower systemic blood pressure, the lowering of pulmonary arterial blood pressure, the ability to vasodilate arteries and fight against ischemic heart diseases, cardiac failure, peripheral arterial disease and cerebral vasospasm, the ability to down regulate acute inflammation, promoting sleep, and the ability to restore various neurodegenerative deficits.

The adenosine monophosphate complexes of the instant invention also have vasodilating properties and can be used in similar indications.

The adenosine triphosphate complexes of the instant invention have pharmacological activities including, vasodilation, the ability to inhibit various tumor growth, the ability to enhance the efficacy of cancer chemotherapy, the ability to fight muscular fatigue including that of heart failure, the ability to fight weight loss.

Most of these different pharmacological effects are thought to be mediated by adenosine and ATP specific receptors. For this purpose molecules of the present invention may be provided in any form enabling oral administration (in particular in the form of gel capsules, drinkable solutions or emulsions, powders, gels, lozenges, tablets), nasally (for example solutions administered in the form of drops or sprays), in the form of collyrium (eye drops or solutions) by the pulmonary route (solutions in pressurized aerosol dispensers), rectally (suppositories) cutaneously (for example ointments or transdermal devices also known as patches) or transmucosally for example sublingually (solutions in pressurized dispensers or tablets that crumble in the mouth) or vaginally (particularly vaginal creams or suppositories) or by the intravenous, subcutaneous, intramuscular routes (injectables suspensions or solutions).

Delivery of the complexes into the brain can be done via nanoparticles made of safe ingredients below 400 nanometers or using liposomes and PEGlyated immunoliposomes systems.

EXAMPLE 1 a. Complexing of Adenosine with Para-Aminobenzoic Acid and Dimethylaminoisopropanol (Adb011).
  The synthesis of this compound follows a two step process:
  Step 1: synthesis of compound 330A1 (FIG. 1).
  The suspension of compounds 330A0 (4-acetamidobenzoic acid, a para-aminobonzoic acid derivative) and 330B0 (dimethylaminoisopropanol) in water is stirred for 2 hours at 50° C. The solvent is evaporated under vacuum. The residue is taken up and evaporated three times in acetonitrile. The residue is taken up in cold acetonitrile, crystallization is observed. The solid is filtered and dried under vacuum. Compound 330A1 (salt) is obtained as a white solid (approximately 6 g.) The yield is approximately 76% the purity of compound 330A1 is controlled by RMN 1H and is approximately greater than 95%. See FIG. 1 for quantities and for chemical structures.
  Step 2: synthesis of final compound 330A2 currently named Adb011 (FIG. 1).
  Compounds 330A1 (salt) and 320A0 (adenosine) are added to water at room temperature (RT). The mixture is stirred at RT for three hours. The formation of a precipitate is observed (paste). Water is added until stirring is observed again. The mixture is evaporated under vacuum to yield 2.1 g. of compound 330A2 as a white solid. Yield is approximately 100%. The purity of compound 330A2 is controlled by RMN 1H and is approximately greater than 95%. See FIG. 1 for quantities and chemical structures.
b. Complexing of Adenosine Triphosphate with Para-Aminobenzoic Acid and Dimethylaminopropanol (Adb311)
  This complex is produced by the same process as shown above, see FIG. 2.
c. Complexing of Adenosine Monophosphate with Para-Aminobenzoic Acid and Dimethylaminopropanol (Adb111)
  This complex is produced by the same process as shown above, see FIG. 2.
d. Complexing of Adenosine with Adipic Acid and Dimethylaminopropanol (Adb013)
  This complex is produced by the same process as shown above, but different intermediary product. See FIG. 3a.
e. Complexing of Adenosine with Acetyl Salicylic Acid and Dimethylaminopropanol (Adb-012).
  This complex is produced by the same process as shown above, but different intermediary product. See FIG. 3b.
f. Complexing of Adenosine Monophosphate with Acid Acetyl Salicylic and Dimethylaminopropanol (Adb-112)
  This complex is produced by the same process as shown above, but different intermediary product. See FIG. 3c.

One of skill in the art will recognize that the above components can be replaced by substitute or equivalent components (see FIG. 3/FIGS. 1 & 2). For example, other amino alcohols may be used in varying proportions. One of skill in the art would further recognize that changes in the amino alcohols and their ratios could affect the characteristic of the resulting compound.

EXAMPLE 2

Infrared Spectrum Analysis of Adenosine, AMP and ATP Complexes

The following spectra were recorded on the same apparatus with the same operating protocol.
1. Spectrum of the complexes (Adb011, Adb111, Adb311).
2. Spectrum of the mixtures adenosine/salt, AMP/salt, ATP/salt: ⅓. (Salt of the example is 330A1).
3. Comparison of the spectra was then analysed by the computer.

Between wave number 2800 $cm^{-1}$ and 1800 $cm^{-1}$, no difference is shown between Adb011, Adb111, Adb311 and their original components. Between 3600-3200 $cm^{-1}$, and 1700-500 $cm^{-1}$, curves of the three compounds and that of their original components are very different. See FIGS. 4 to 9

This experiment confirms the formation of complexes between aminoalcohol-acetamidobenzoic acid salt and adenosine or AMP or ATP.

EXAMPLE 3

The Effect of Oral Administration of Adb011 on Blood Pressure of Normotensive Wistar Rats The experiment was performed in 10 male Wistar rats (340 to 410 g; 5 in the treated group and 5 in the control group). Animals were maintained for two weeks of adaptation in humidity and temperature controlled room and were fed a standard diet (U.A.R, Villemoisson, France). Each animal, (control or treated) was anaesthetized with sodium pentobarbital (6%, 0.9 ml/Kg body weight). The left carotid artery was cannulated with a PE50 polyethylene catheter connected to a pressure transducer (MacLabs, ADInstruments, Hastings, UK). Blood pressure was monitored continuously and recorded. Adb011 was administered orally by gavage at the dose of 50 mg/kg (in Arabic syrup 5%).

Results are reported as mean±SEM of n experiments. Multiple measurement analysis was performed using ANOVA, followed by Bonferroni-Dunn test. Statistical significance was accepted for p values less than 0.05. The results are shown in FIG. 10.

FIG. 10 shows mean values of blood pressure (±SEM) in 5 rats receiving 50 mg/kg Adb011 p.o. (n+5) and 5 rats receiving vehicle (control group). Blood pressure began to decrease after 30 minutes of Adb-011 administration. It reached a significant maximal decrease of −13.9 mmHg between 70 and 100 min. (with respect to vehicle values, p<0.05 ANOVA multiple measurement analysis followed by a Bonferroni-Dunn test) and returned to normal after 110-120 minutes. In the control group, blood pressure slightly decreased due to anesthesia conditions.

In conclusion, orally administered Adb-011 effectively lowered blood pressure in rats for up to 110-120 min beginning 30 minutes after administration suggesting that it crosses the gastrointestinal barrier and delivers adenosine in the body for up to two hours See FIG. 10.

EXAMPLE 4

Effects of Abd011 by the IV Route on Systemic Arterial Pressure in Rats

The experiment is similar to example 3.

Experimental Protocol

Animals were divided in two groups:
  Adb-011 (n=4): receiving IV a bolus of Adb-011 (10 mg/kg in suspension with distilled water 30 mg/ml)
  Control (n=3): receiving IV (distilled water)

FIG. 11 shows mean values of blood pressure (±SEM) in the treated group (Adb011-10 mg) and control group (vehicle). In the treated group, blood pressure began to decrease after 15 min of the Adb011 administration and reached a significant maximal decrease of 48 mmHg at 15 minutes. In the control group, blood pressure slightly decreased beginning after the administration of sodium pentobarbital and then leveled off.

Results demonstrate that Adb011 administered IV has a very strong and prolonged effect on mean arterial blood pressure which is still very low two hours after injection. Given that Adb-011 is a slow releasing form of adenosine, one should also compare these results with the well documented duration of activity of natural adenosine administered under the same conditions and which is less than one minute.

EXAMPLE 5

The Effect of Oral Administration of Adb011 on Chronic Pulmonary Hypertension Caused by Hypoxia on Rats.

The adenosine compound (Adb-011) was tested for its ability to reduce pulmonary artery pressure in hypoxic rats (rats exposed to chronic hypoxia, Pb=380 mmHg, for 14 days). Animals were divided in three groups:
  Adb-011 chronic treatment (n=5): receiving by gavage Adb-011 (50 mg/kg in suspension with Arabic syrup, 20 mg/ml) twice a day (morning and evening) for 14 days.
  Control (n=6): receiving by gavage vehicle (suspension of Arabic syrup 20 mg/kg).
  Adb-011 acute treatment (n=6): receiving by gavage vehicle for 14 days and orally treated with a single dose of Adb-011 on the last day (day of surgery).

Rats were placed in a chamber where air was circulated at a pressure of 380 Torr, which corresponds to an altitude of 5500 meters. The chamber was open twice a day for ~30 minutes to treat animals and to replace food and water.

On the day of surgery the animals were removed from the chamber and anesthetized with pentobarbital sodium (60 mg/kg ip). A polyethylene catheter (PE-50) was placed in the aortic arch via the left carotid artery. An introducer was advanced in the right ventricle via the right jugular vein. Adequate placement of both catheters was established by the pressure waveform. Both catheters were connected to a pressure transducer (Biopac MP30, BIOPAC Systems, Inc.). The time-lag between last dose of Adb-011 (in group 1) and blood pressure measurement was 14 hours.

Results and conclusions: Adb-011 given twice a day significantly decreased pulmonary hypertension ((by 21.5 mmHg) and right ventricular hypertrophy (−75 mg) induced by chronic hypoxia, with no effect on systemic pressure. Acute administration of Adb-011 in rats with fixed pulmonary hypertension was also able to reduce pulmonary artery pressure (−22 mmHg). See FIG. 12. Results of all measurements are shown in Table 1.

TABLE 1

|  | HxC | HxA | HxC + A 15 min | HxC + A 60 min |
|---|---|---|---|---|
| RVp (mmHg) | 74.80 ± 3.43 | 53.30 ± 461* | 75.17 ± 0.95 | 52.83 ± 3.83 # |
| HR (beat/min) | 358 ± 21 | 364 ± 15 | 352 ± 12 | 329 ± 4 |
| MABP (mmHg) | 109 ± 6 | 113 ± 2 | 107 ± 5 | 92 ± 5 # |
| Cardiac output (mL/min/kg) | 182 ± 14 | 162 ± 8 | 164 ± 11 |  |
| SVR | 0.61 ± 0.05 | 0.70 ± 0.03 | 0.68 ± 0.06 |  |
| SV (mL/kg) | 0.51 ± 0.04 | 0.45 ± 0.02 | 0.47 ± 0.03 |  |
| SaO2 (%) | 77 ± 7 | 92 ± 1* | 82 ± 4 |  |
| CaO2 (mL O2/dL of blood) | 25.1 ± 2.2 | 29.2 ± 0.9 | 27.3 ± 1.4 |  |
| CvO2 (mL O2/dL of blood) | 18.2 ± 2.2 | 21.2 ± 1.0 | 19.0 ± 1.5 |  |
| C(a − v)O2 (mL O2/dL blood) | 6.8 ± 0.3 | 8.0 ± 0.4 | 8.3 ± 0.5 |  |
| VO2 (mL/min/kg) | 12.28 ± 0.52 | 12.81 ± 0.29 | 13.38 ± 0.61 |  |
| BW (g) | 293 ± 2 | 294 ± 5 | 303 ± 3 |  |
| RVw (mg) | 437 ± 24 | 362 ± 10* | 436 ± 21 |  |

TABLE 1-continued

|  | HxC | HxA | HxC + A 15 min | HxC + A 60 min |
|---|---|---|---|---|
| (LV + S)w | 644 ± 26 | 729 ± 56 | 675 ± 21 | |
| Fulton' ratio | 0.681 ± 0.039 | 0.506 ± 0.033 | 0.645 ± 0.019 | |

$p < 0.05$, HxA vs HxC, HxC + A 15 min;
$p < 0.05$, HxC + A 60 min vs HxC + A 15 min.
HxC: Hypoxic control group;
HxA: hypoxic adenosine group;
HxC + A: hypoxic treated by Adb-011 the day of the surgery
RVp: Right ventricular pressure;
HR: heart rate;
MABP: mean arterial blood pressure;
SVR: systemic vascular resistance;
SV: stroke volume;
SaO2: arterial oxygen saturation;
CaO2: arterial O2 content;
CvO2: Venous O2 content;
C(a − v)O2: arterial − venous O2 difference;
VO2: Oxygen consumption;
BW: body weight;
RVw: right ventricular weight;
(LV + S)w: left ventricular + septum weight

EXAMPLE 6

The Effect of Oral Administration of Adb111 (AMP Complex) on Blood Pressure of Normotensive Wistar Rats and Comparison with AMP The experiment is similar to example 3.

Experimental Protocol

Animals were divided in five groups:
- Adb-111-I (n=5): receiving by gavage Adb-111 (100 mg/kg in suspension with Arabic syrup 30 mg/ml).
- AMP-I (n=5): receiving by gavage Adenosine monophosphate (100 mg/kg in suspension with Arabic syrup 30 mg/ml).
- Adb-111-II (n=5): receiving by gavage Adb-111 (300 mg/kg in suspension with Arabic syrup 30 mg/ml).
- AMP-II (n=5): receiving by gavage Adenosine monophosphate (300 mg/kg in suspension with Arabic syrup 30 mg/ml).
- Control (n=4): receiving by gavage Arabic syrup 30 mg/ml alone.

In the two groups treated by Adb111-100 mg and Adb111-300 mg, blood pressure began to decrease after 45 min of the Adb-111 administration and returned to normal values after 180 min.

In the two groups treated by AMP-100 mg and AMP-300 mg, blood pressure began to decrease after 45 min of the AMP administration and returned to normal values after 120 min. The decrease was maximal in between 75 and 120 min for Adb111-100 mg/and after 60 min and 90 min for Adb111-300 mg.

The drop in Adb111 groups is significant when compared to blood pressure values in the control group (p<0.05). It is also significant and longer in duration when compared to AMP curves. Indeed no differences were shown between Adb-111 and AMP at the beginning of the experiment but after 45 minutes the effect was stronger with Adb-111 and ultimately lasted longer. The mean arterial blood pressure was significantly lower in Adb111-100 mg/kg between 90 and 135 minutes and in Adb111-300 between 75 and 150.

Given that Adb111 provides 3.3 times less AMP than natural AMP at the same dosage, one should actually compare Adb111-300 mg to AMP-100 mg. Under those conditions the difference between the two products appears even more clearly and is more significant. In the control group, blood pressure decreased only slightly likely due to anesthesia conditions. See FIG. 13.

In conclusion, orally administered Adb-111 effectively lowered blood pressure in rats for up to 165 min beginning 45 minutes after oral administration thus suggesting that it crosses the gastrointestinal barrier and delivers adenosine monophosphate in the circulation for up to two hours.

Oral AMP also lowered blood pressure in rats for 60 minutes but to a much lesser extent. This indicates that Adb111 crosses the GI and is more capable than natural AMP to achieve active circulating pharmacological concentrations. Overall, Adb111 shows a better bioavailability and efficacy over natural AMP at comparable doses. See FIG. 13.

EXAMPLE 7

The Effect of Oral and IV 330A1 (Preferred Salt of the Complexes) on Blood Pressure of Normotensive Wistar Rats The experiment is similar to example 3.

Animals were divided in four groups:
- 330A1-I (n=4): receiving by gavage the product (50 mg/kg in suspension with Arabic syrup 30 mg/ml)
- Control-(n=4)I: receiving by gavage Arabic syrup 30 mg/ml alone
- 330A1-II: receiving the product IV (10 mg/kg in suspension with distilled water 30 mg/ml)
- Control-II (n=4): receiving IV distilled water Results can be seen in FIG. 14. They demonstrate that 330A1 has a minor effect on mean arterial blood pressure, not very different from control and thus does not account for Adb011 and Adb111 strong effects on mean arterial blood pressure. These are likely to be due to the release of adenosine and AMP respectively.

While the invention has been described with reference to certain exemplary embodiments thereof, those skilled in the art may make various modifications to the described embodiments of the invention without departing from the scope of the invention. The terms and descriptions used herein are set forth by way of illustration only and are not meant as limitations. In particular, although the present invention has been described by way of examples, a variety of compositions and methods would practice the inventive concepts described herein. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A composition comprising a complex of adenosine or an adenosine phosphate with dimethylaminoisopropanol.

2. A composition comprising a pharmacologically active salt of a complex of an adenosine phosphate with an amino-alkanol.

3. The composition of claim 2, wherein the amino-alkanol is dialkylamino-alkanol.

4. The composition of claim 2, wherein the salt is formed with para-aminobenzoic acid.

5. The composition of claim 2, wherein the salt is formed with 4-acetamidobenzoic acid.

6. The composition of claim 2, wherein the salt is formed with aspirin.

7. A composition comprising a complex of adenosine with an amino-alkanol selected from among the group consisting of: diethylaminoethanol, diethylaminoisopropanol, methylethylaminoethanol, dimethylaminopropanol, dimethylaminobutanol, dibutylaminoethanol, dipropylaminoethanol, and diisopropylaminoethanol.

8. The composition of claim 7, wherein the mole ratio of adenosine to amino-alkanol is about 1:1 to 1:10.

9. A composition comprising a pharmacologically active salt of a complex of adenosine with an amino-alkanol selected from among the group consisting of: dimethylaminoisopropanol, diethylaminoethanol, diethylaminoisopropanol, methylethylaminoethanol, dimethylamino propanol, dimethylaminobutanol, dibutylaminoethanol, dipropylaminoethanol, and diisopropylaminoethanol.

10. The composition of claim 9, wherein the salt is formed with para-aminobenzoic acid.

11. The composition of claim 9, wherein the salt is formed with 4-acetamidobenzoic acid.

12. The composition of claim 9, wherein the salt is formed with aspirin.

* * * * *